United States Patent
Ishii

(12) 
(10) Patent No.: US 6,603,057 B1
(45) Date of Patent: Aug. 5, 2003

(54) HETEROGENOUS AND HOMOGENEOUS MOUSE VARIANTS LACKING SNO GENE

(75) Inventor: Shunsuke Ishii, Ami-machi (JP)

(73) Assignees: Japan Science and Technology Corporation, Saitama-Ken (JP); Riken, Saitama (JP)

( * ) Notice: Subject to any disclaimer, the term of this patent is extended or adjusted under 35 U.S.C. 154(b) by 0 days.

(21) Appl. No.: 09/936,357

(22) PCT Filed: Nov. 24, 1999

(86) PCT No.: PCT/JP99/06541

§ 371 (c)(1), (2), (4) Date: Sep. 11, 2001

(87) PCT Pub. No.: WO00/53005

PCT Pub. Date: Sep. 14, 2000

(30) Foreign Application Priority Data

Mar. 11, 1999 (JP) .............................................. 11/64372

(51) Int. Cl.⁷ ........................ G01N 33/00; A01K 67/027
(52) U.S. Cl. ............................................. 800/3; 800/18
(58) Field of Search ........................................ 800/18, 3

(56) References Cited

PUBLICATIONS

Wall, Transgenic livestock: Progress and prospects for the future, 1996, Theriogenology, vol. 45, pp. 57–68.*

Sigmund, Viewpoint: Are studies in genetically altered mice out of control?, 2000, Arterioscler Thromb. Vasc. Biol., vol. 20, pp. 1425–1429.*

Nomura N. et al., Nucleic Acids Res., vol. 17(14), p. 5498–5500 (1989).

Capecci M. R. et al., Trends in Genetics, vol. 5(3), p. 70–76 (1989).

Nomura T. et al., Genes & Development, vol. 13, p. 412–423 (1999).

Cohen S.B. et al., Oncogene, vol. 17 p. 2505–2531 (1998).

Kano K. et al., J. Reprod. Dev., vol. 44(3), p. 253–260 (1998).

Pearson–White S. et al., Nucleic Acids Res., vol. 25 (14), p. 2930–2937 (1997).

* cited by examiner

*Primary Examiner*—Anne-Marie Falk
*Assistant Examiner*—Daniel M. Sullivan
(74) *Attorney, Agent, or Firm*—Peter F. Corless; Christine C. O'Day; Edwards & Angell, LLP

(57) ABSTRACT

Functions of sno gene are analyzed by constructing heterogenous or homogeneous mouse variants lacking sno gene to thereby provide heterogenous or homogeneous mouse variants lacking sno gene, cells of these animals and screening systems with the use of these animals or cells. Non-human animals, preferably mice, lacking sno gene and cells thereof. The above animals or cells thereof include both of heterogenous variants and homogenous variants. A method for screening candidates for drugs by using the above animals or cells thereof.

5 Claims, 6 Drawing Sheets

Colony formation in methylcellulose gel

| mEF | | – | v-Ki-ras |
|---|---|---|---|
| E14-1 | (+/+) | 0* | 0.0 ± 0.0 |
| E14-2 | (+/+) | 0 | 0.7 ± 0.6 |
| E14-3 | (+/+) | 0 | 0.3 ± 0.6 |
| E14-6 | (+/+) | 0 | 0.3 ± 0.5 |
| E14-4 | (+/−) | 0 | 72.3 ± 6.3 |
| E14-7 | (+/−) | 0 | 85.3 ± 8.5 |
| E15-1 | (+/−) | 0 | 57.7 ± 9.8 |
| E15-2 | (+/−) | 0 | 31.6 ± 7.9 |

*: number of colony / 1000 cells

HETEROGENOUS AND HOMOGENEOUS MOUSE VARIANTS LACKING SNO GENE

TECHNICAL FIELD

The present invention relates to non-human animals, preferably mice, lacking the sno gene and cells thereof, preferably embryos thereof, or a method for screening substances by using the above animals or cells thereof.

BACKGROUND ART

A coactivator such as CBP, and a corepressor such as N-CoR, are called as "mediating factors". The mediating factors were identified as molecule which acted as a bridge between the transcriptional regulatory factor binding to the enhancer/silencer upstream of the promoter and a basal transcription factor, such as TBP, binding to the core promoter. The mediating factors form complexes with histone acetyltransferase (HAT, an enzyme acetylating histone) or, on the contrary, with histone deacetylase (HDAC, a deacetylating enzyme from histone), indicating that it changes the chromatin structure through acetylation of histone in order to regulate gene expression. The regulation of gene expression by modifying the chromatin structure is thought to be involved in various life processes such as immunity and development and differentiation, but the mechanisms are unknown.

Ikaros, which was originally thought to be a T cell specific transcriptional activation factor, has been demonstrated, by recent studies of a British group, to recruit a T cell specific gene into the heterochromatin region, which is the transcription inactivated region. It then plays a role in the expression of these genes in undifferentiated cells. As can be understood from this example, gene expression regulation mediated by the chromatin structure is very important in expression and differentiation of the immune system. Consequently, studies on the mediating factors provide a breakthrough in this area.

One of the important matters in discussing the physiological function of the mediating factors is "haploinsufficiency", which means that half is insufficient. Since eucaryotic cells are diploid and normally have two copies of genes, even if a mutation occurs in one copy of the gene, the phenotype does not appear in most cells. Studies by the inventors of the present invention have found that, in the case of the mediating factors, if a mutation occurs in one copy of the gene, the amount of gene product reduces to half. This process connects directly with an abnormal phenotype.

This leads to the idea that, since limited types and numbers of the mediating factors are commonly used for large numbers of the transcriptional regulatory factors, the reduction in the amount of gene product to half is directly related to the abnormal phenotype. Consequently, diseases which develop as a result of a mutation in the mediating factors gene commonly occur in the group of so-called "autosomal dominant diseases (which mean onset occurs as a result of a mutation of one copy of the gene in an autosome)", and they frequently result in a disease.

N-CoR was originally identified as a corepressor which is essential for transcriptional regulation of the action of the intranuclear hormone receptor and, together with a factor such as Sin3 or HDAC, constitutes a large complex. We have analyzed the physiological function of ski/sno, a constitutional factor of the N-CoR corepressor complex.

The ski gene was originally found as an oncogene which transforms the chicken embryonic fibroblastoma cells (Stavnezer, E., et al., Mol. Cell Biol., 9, 4038–4945, 1989). We have found that the protein encoded by the c-ski gene and its related gene sno (Nomura, N., et al., Nucleic Acid Res., 17, 5489–5500, 1989) bind to the corepressor N-CoR/SMRT (Hoerlein, A. J., et al., Nature, 377, 397–404, 1995; Chen, J. D., et al., Nature, 377, 454–457, 1995), and to mSin3 (Ayer, D. E., et al., Cell, 80, 767–776, 1995; Screiber-Agus, N., et al., Cell, 80, 777–786, 1995), and form a complex with histone deacetylase (HDAC).

Ski/Sno is essential for the transcriptional repression which is mediated by thyroid hormone receptor and Mad. Further, these are directly bound with Rb as well as requiring an Rb-mediating repressive factor.

We have found that Ski, which was identified as an oncogene product, and its related gene product Sno, bind directly with N-CoR and Sin3 to function as the constitutional factor of the N-CoR complex. Quite interestingly, the transcriptional suppression generated by the tumor suppressive gene products Mad and Rb require Ski/Sno. Heterogeneous mice lacking Sno were prepared and a carcinogenesis experiment was conducted. As a result, we have found that these mice were highly cancer-prone, and it was shown for the first time that the Ski/Sno gene family was a tumor suppressor gene. In addition, heterogeneous mice lacking sno exhibit various abnormalities in their immune systems. The mice have extraordinarily high levels of induced Th1 group cytokines such as interferon $\gamma$, and easily develop ulcerative colitis. The germinal center does not form in these mice and induction of B cell proliferation by LPS is not observed. We have also examined the relationships between various abnormalities and diseases observed in mice in which the amount of Ski or Sno is reduced to half the normal level, and their molecular mechanisms.

An object of the present invention is to provide heterogeneous or homogeneous mouse variants lacking the sno gene and cells of these animals by constructing heterogeneous or homogeneous mouse variants lacking sno gene and analyzing functions of sno gene.

Another object of the present invention is to provide screening systems involving the use of these animals or their cells.

DISCLOSURE OF THE INVENTION

The present invention includes non-human animals, preferably mice, lacking sno genes and cells thereof. The animals lacking sno gene and cells thereof of the present invention include both heterogeneous variants and homogeneous variants.

Further, the present invention relates to a method for screening candidates for drugs by using the above animals or cells thereof.

(b) a photograph instead of a drawing showing lymphoma of mice developed tumor. (c) a photograph instead of a drawing showing metastasis to thymus. (d) a photograph instead of a drawing showing anti-TCR β (T cell receptor α and β) positive tumor. (e) a photograph instead of a drawing showing that tumor is not positive for B-cell marker IgM. (f) a photograph instead of a drawing showing tumor of pancreas of mice developed tumor. (g) and (h) photographs instead of drawings showing results of immunostain of mouse B lymphoma using T-cell and B-cell specific antibodies.

Figure 5A:
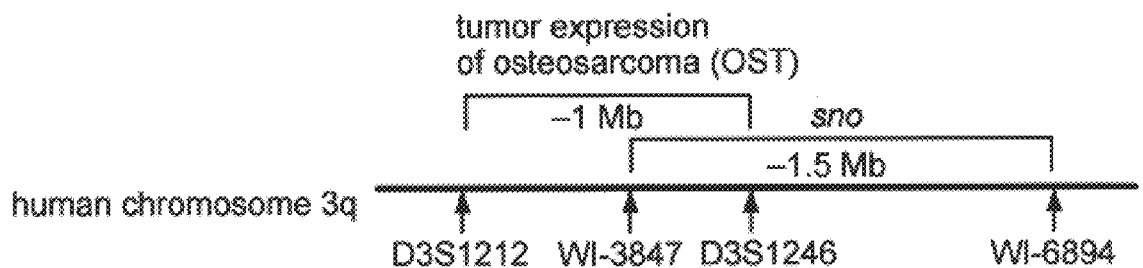
Figure 5B:
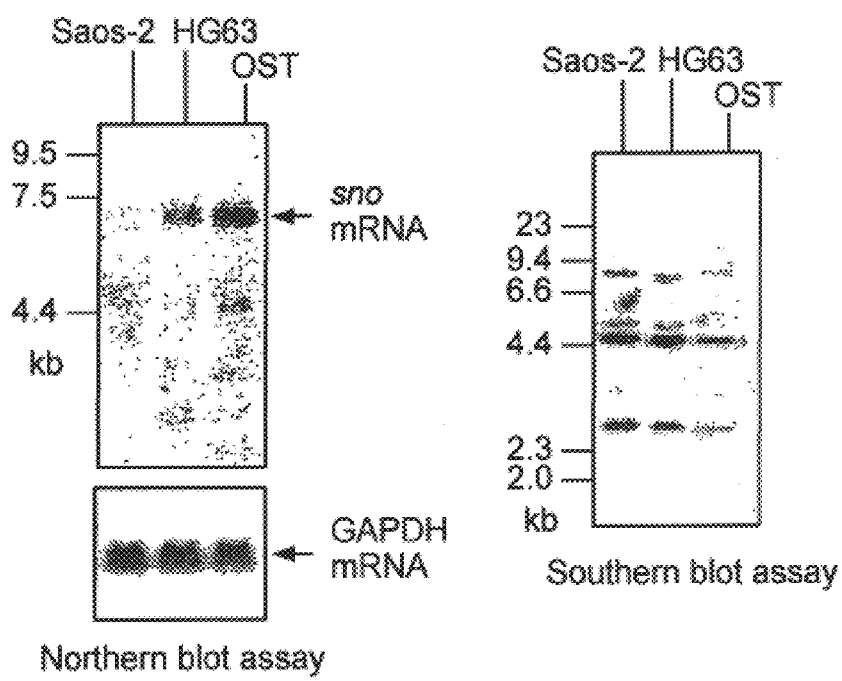

FIGS. 5A and 5B: (a) shows loci in chromosome of human sno. (b) photographs instead of drawings showing results of assays in expression of m-RNA of sno gene of three type cells, i.e. Saos-2, HG63 and OST.

BEST MODE FOR CARRYING OUT THE INVENTION

The method for preparing non-human animals lacking the gene of the present invention is described using mice as an example.

The sno mutant mice were developed by homologous recombination of embryonic stem cells (ES cells).

Figure 1A:
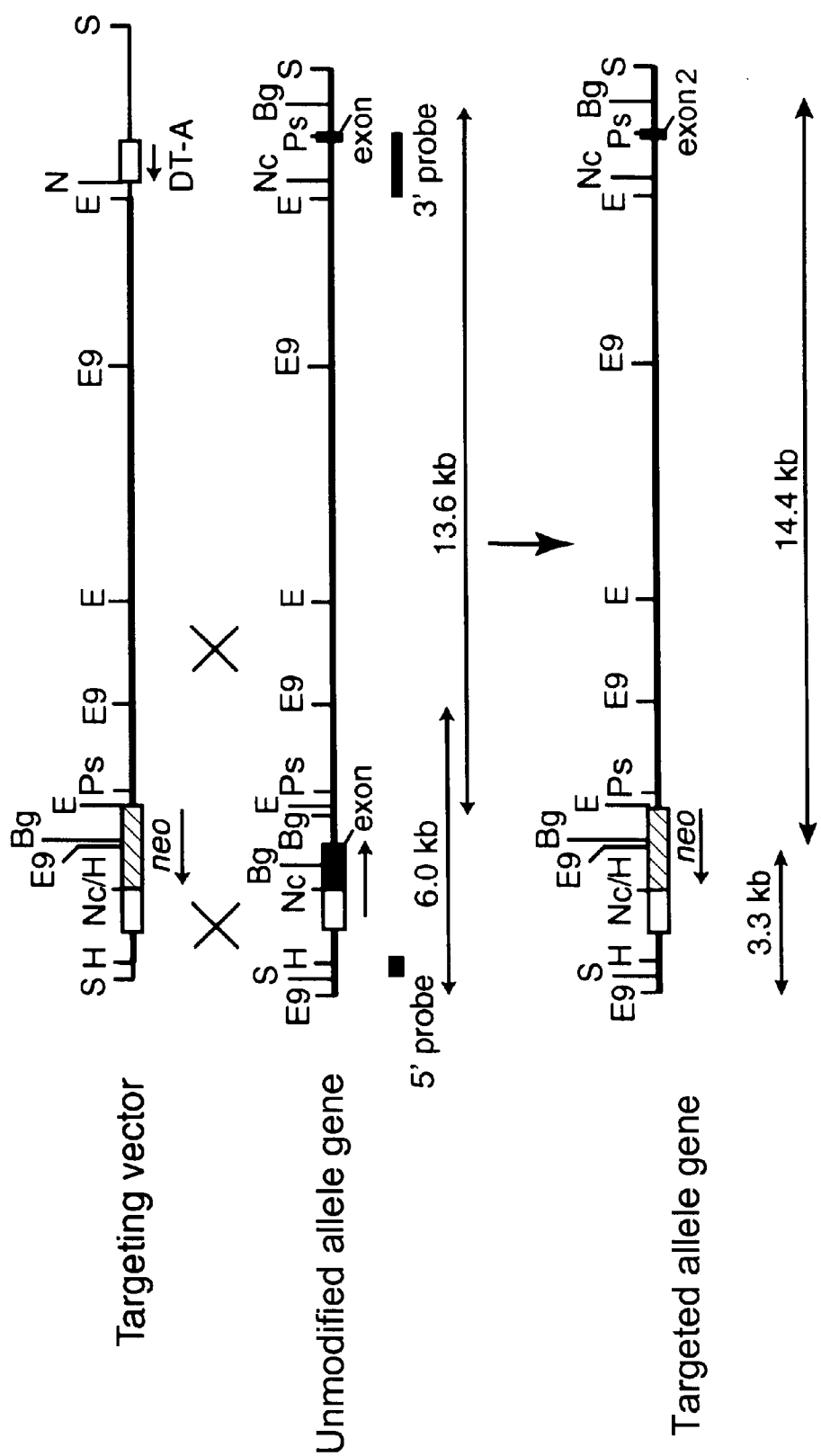
FIGS. 1A and 1B: (a) shows restriction maps of vector and allele gene used in the present invention. (b) shows photographs instead of drawings showing results of analyses confirming expression in each genotype.

A gene-targeting vector in the exon region encoding amino acids 1–362 of SnoN, which is one of the multiple Sno protein species generated by alternative splicing, was replaced by a neo cassette [refer to FIG. 1(a)]. Homologous recombinants were characterized by the appearance of a 3.3 kb EcoO1091 fragment using the 5' probe, and a 14.4 kb BglI fragment using the 3' probe [refer to FIGS. 1(a) and (b)]. The chimeras were normally obtained from two independent mutant ES clones.

Figure 1B:
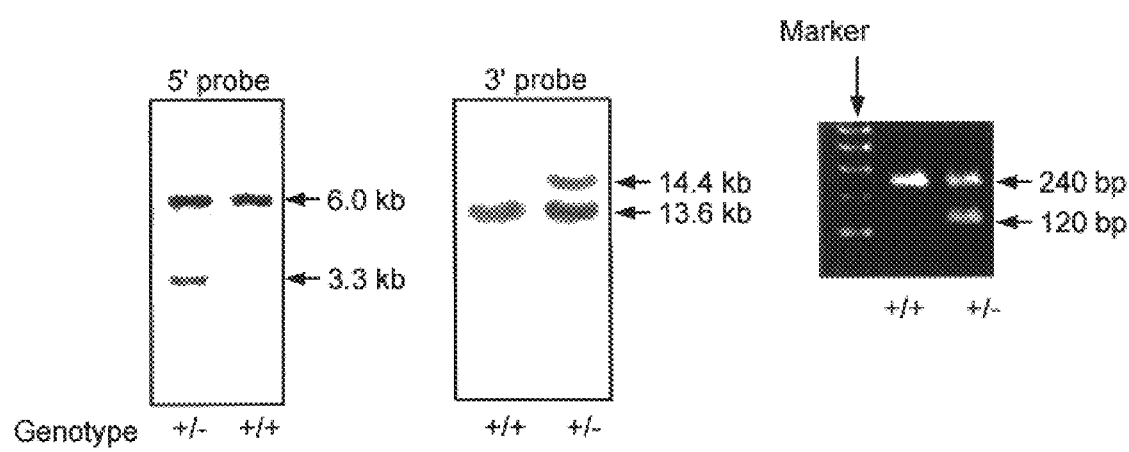

The chimeras were mated with C57BL/6 or BALB/c females in order to generate F1 heterozygous mutant mice. Heterozygous mice were identified by PCR and Southern blot analyses of genomic DNA isolated from tail samples of the offspring [refer to FIG. 1(b)]. Heterozygous mice were crossed, and the genotypes of the resulting 3 week old offspring were determined. Among 211 offsprings derived from two independent germ-line chimeras, no $sno^{-/-}$ homozygotes were detected and the ratio of the $sno^{+/+}$ to the $sno^{+/-}$ genotype was 1:2. The fact that the ratio of the $sno^{+/+}$ to the $sno^{+/-}$ genotype in the progeny population was 1:1 in the cross of the $sno^{+/-}$ and the $sno^{+/+}$ (either female or male), indicated that the sno germ cells were not eliminated during spermatogenesis or oogenesis.

To identify the time at which the $sno^{-/-}$ animals died, postimplantation embryos (E3.5–E16.5) from heterozygous matings were surgically explanted from the uterine tissue of pregnant females and their genotype was identified by PCR. No $sno^{-/-}$ embryos were obtained after E3.5.

Figure 2:
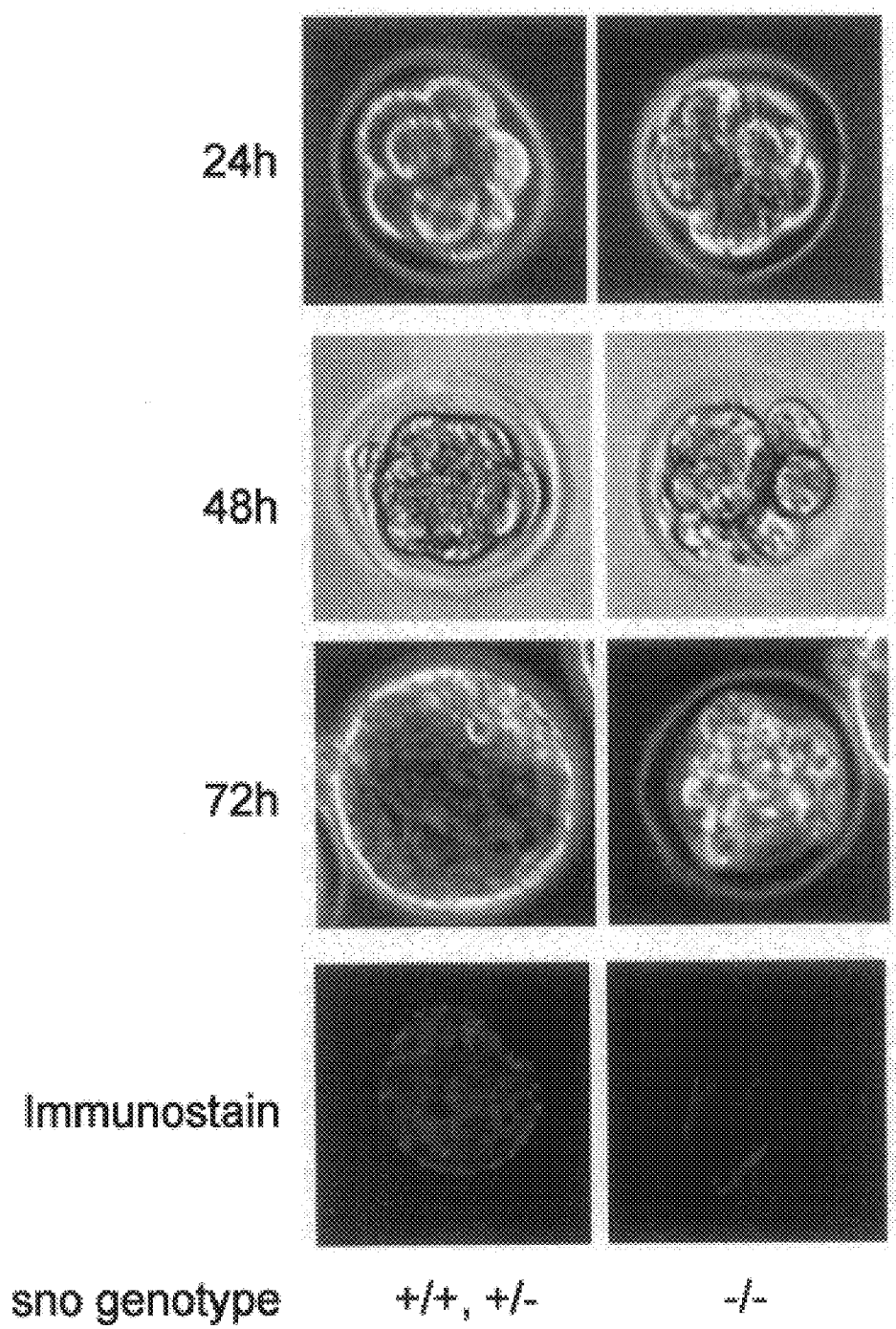
FIGS. 2: Photographs instead of drawings showing results of immunostain in each genotype.

To characterize the preimplantation development of the $sno^{-/-}$ embryos, 2-cell embryos derived from heterozygous xenogeneic crosses at E1.5 were recovered and cultured individually. Their development was monitored every 12 to 24 hours. The developmental potential of each embryo was correlated with the presence of the Sno protein. The presence of Sno protein was scored by immunostaining with Sno-specific antibodies. About 25% of the embryos (n=20) exhibited no significant staining. All of these had a defect in blastocyst formation (refer to FIG. 2, right column). These embryos cleaved normally to the 8-cell stage during the first 24 hours in culture.

However, they became decompacted during the second and third days in culture, and failed to divide beyond approximately the 16-cell stage or to form a blastocoel. The remaining embryos were strongly labeled for Sno and developed into normal blastocysts (refer to FIG. 2, left column). These results indicate that sno is required for blastocyst formation. Since ski-deficient mice were alive even at E18.5 (Berk, M., et al., Genes Dev., 11, 2029–2039, 1997), ski and sno have different roles during development.

Ski overexpression in cultured cells is accompanied by growth inhibition (Colmenares, C., et al., Cell, 59, 293–303, 1989). In addition, normal c-Ski and Sno are both required for transcriptional repression by Mad and Rb which negatively regulate cellular proliferation. To investigate the possibility that sno negatively regulates cellular proliferation, we studied the growth of early passages of mouse embryonic fibroblasts (MEFs) prepared from E15.5 embryos, which express sno normally.

Figures 3A, 3B:
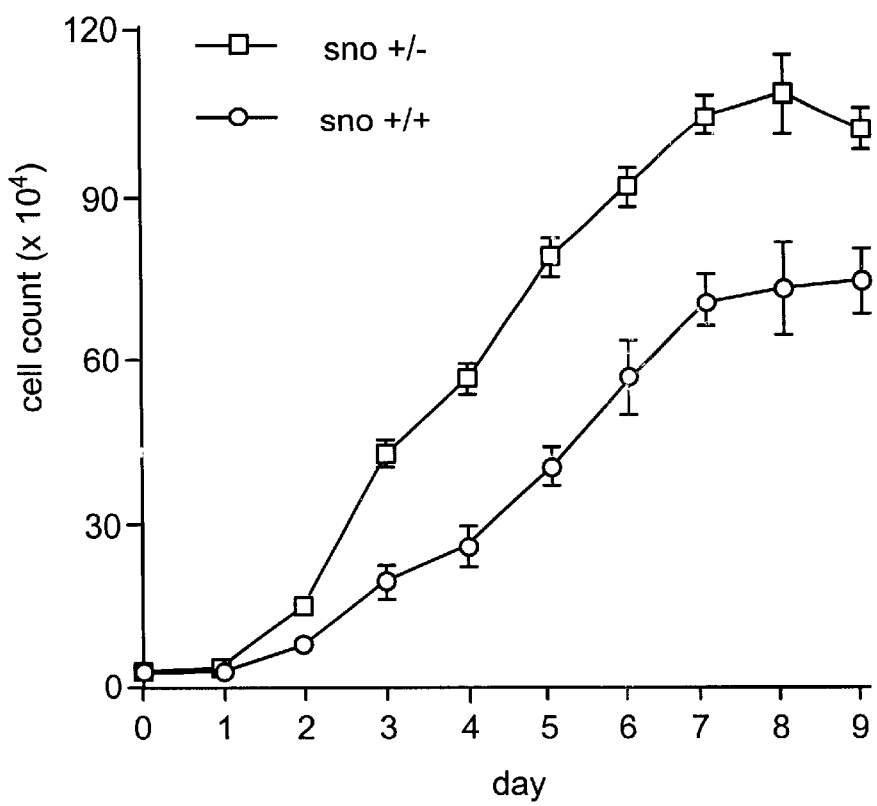
FIGS. 3A and 3B: (a) shows a graph showing growth of cells in each genotype. (b) shows numerical indication of colony formations of each genotype in methylcellulose gel after infection with oncogenic virus.

Although $sno^{+/+}$ and $sno^{+/-}$ cultures were morphologically indistinguishable at low density, $sno^{+/-}$ MEFs grew faster than wild-type MEFs [refer to FIG. 3(a)]. In addition, $sno^{+/-}$ MEF monolayers achieved higher cellular densities [refer to FIG. 3(a)]. To determine the basis for their increased proliferating capacity, we assayed the cell-cycle profile of wild type and $sno^{+/-}$ MEFs.

In the $sno^{+/-}$ samples, we observed an increased expression during the $G_1$ phase of the cell cycle which was proportional to the increase in proliferating capacity (data not shown). In order to further study the ability to complete full transformation, colony formation in methylcellulose was examined. After infection with a virus carrying the v-K-RAS oncogene, the $sno^{+/-}$ MEFs generated 32–85 colonies per 106 cells, whereas wild-type MEF generated no colonies at all [refer to FIG. 3(c)].

Thus the loss of one copy of the sno gene allowed the activation of, ras-mediated transformation in cell culture.

Figure 4A:
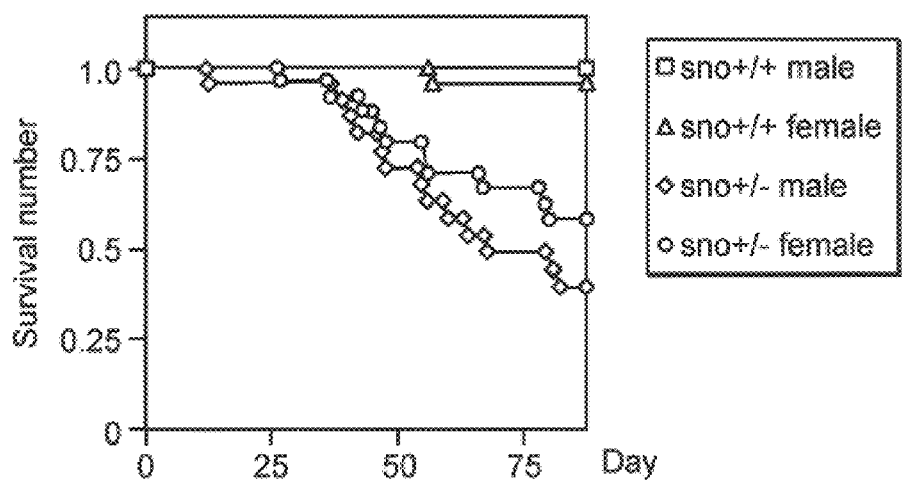
FIGS. 4A–H: (a) a graph showing survival numbers of each genotype after administration of carcinogen DMBA.
Figure 4B:
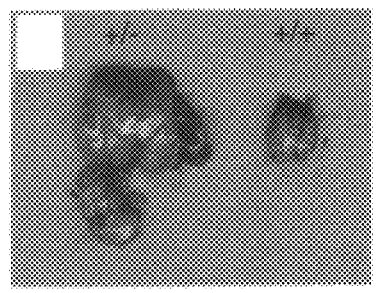
Figure 4C:
Figure 4D:
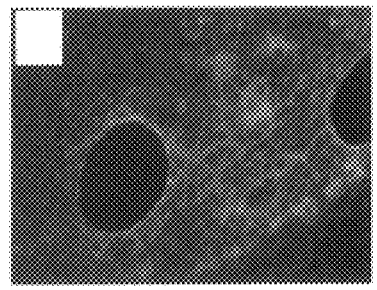
Figure 4E:
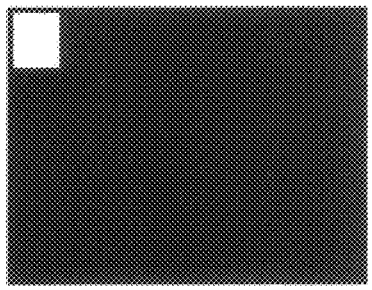

In the next experiment, in order to compare the tumor susceptibility of wild type and $sno^{+/-}$ mice, the carcinogen 9,10-dimethyl-1,2-benzanthracene (DMBA) was administered every week. Over the observation period of 80 days, most of the wild-type mice (n=40) survived even this treatment, but only 30% of the $sno^{+/-}$ female mice (n=20) and 50% of the $sno^{+/-}$ male mice (n=20) survived this treatment, The remaining mice produced clinically apparent tumors [refer to FIG. 4(a), p=0.004]. The major tumor type observed was malignant lymphomas, and fibromas were also found at a lower frequency. Lymphomas in $sno^{+/-}$ mice were aggressive metastatic malignancies, and generated tumors in the thymus glands [refer to FIGS. 4(b) and (c)]. The fact that these originated from T-cells is due to the tumor cells homogeneously expressing the TCRαβ markers, but not the IgM marker [refer to FIGS. 4(d) and (e)].

Figure 4F:
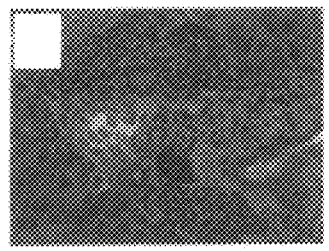
Figure 4G:
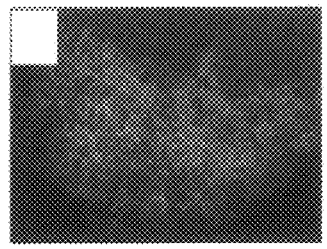
Figure 4H:
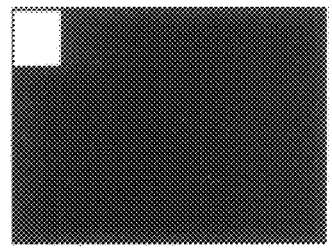

The $sno^{+/-}$ heterozygotes were monitored for the development of tumors in the absence of carcinogen treatment. A predisposition for the development of tumorigenesis was observed to occur at a low frequency in these heterozygotes. One mouse died at the age of 4 months after displaying marasmoid symptoms. Histological analyses of various tissues of this mouse revealed the presence of tumors in the pancreas [refer to FIG. 4(f)]. Immunostaining using T-cell and B-cell specific antibodies indicated that the tumors were B lymphomas [refer to FIGS. 4(g) and (h)]. Generation of lymphomas is very consistent with the fact that introduction of a c-ski expression vector correlates with differentiation of hematopoietic cells (Namciu, S., et al,. Oncogene, 9, 1407–1416, 1994), and the fact that v-ski can affect the growth of avian hematopoietic cells (Larsen, J., et al., Oncogene, 8, 3221–3228, 1993).

To investigate the possibility that the human sno locus is included in the locus of tumor suppression, the location of the sno gene on the human chromosome was determined by using a GeneBridge 4 radiation-hybrid panel. As a result, the sno gene was localized between the WI-3847 and the WI-6894 markers at 3q26.31–3q36.32 [refer to FIG. 5(a)]. The distance between these two markers can be estimated to be about 1500 kb. Quite interestingly, one of the highest frequencies of deficiency of constitutional heterozygosity for human osteosarcomas is also mapped in this region, between the D3S 1212 and the D3S 1246 markers (Kruzelock, R. P., et al., Cancer Res., 57, 106–109, 1997) [refer to FIG. 5(a)].

These two regions containing the sno gene and the tumor suppressor for osteosarcomas overlap each other.

In order to determine whether or not sno expression is lost in cells derived from osteosarcomas, sno mRNA expression in three proliferative cell lines, Saos-2, HG63 and OST was studied. The sno mRNA was not detected in Saos-2 cells [refer to FIG. 5(b), left panel], but the other two cell lines expressed it at comparable levels to those found in fibroblast cell lines. Southern blot analysis indicated that there was no gross rearrangement in the sno gene in Saos-2 cells [refer to FIG. 5(b), right panel], suggesting that the loss of sno expression may be due to a small deletion, a rearrangement in a narrow region, or a point mutation. It is well known that homozygous alterations occur in sporadic osteosarcomas involving both of the two best characterized tumor suppressor genes, p53 and Rb 1, and that Saos-2 lacks the functional Rb protein (Pompetti, F., et al., J. Cell. Biochem., 63, 37–50, 1996).

Although ski and sno have been thought to be oncogenes, so far the results described above demonstrate that these genes act as tumor suppressor. v-Ski lacks the C-terminal region of c-Ski to which mSin3 binds, suggesting that v-Ski acts as a dominant negative form. The overexpression of not only v-ski but also c-ski transforms chicken embryonic fibroblasts (Colmenares, C., et al., J. Virol., 65, 4929–4935, 1991).

We observe that overexpression of c-Ski and Sno are required for transcriptional repression mediated by the proteins encoded by the two different tumor suppressor genes, Rb and mad (Ayer, D. E., et al., Genes Dev., 7, 2110–2119, 1993; Schreiber-Agus, N., et al., Nature, 393, 483–487, 1998). We also note that the transcriptional repressor activity of these proteins may be decreased in sno heterozygous mutants, and the increased expression of a group of target genes of Rb and Mad could cause a predisposition to tumors.

We have recently found that the loss of one copy of the ski gene in MEFs increases the predisposition to mutation, and that the human c-ski gene is localized at 1p36 (results are not shown here), where the multiple tumor suppressor genes for neuroblastoma were also localized (Cheng, N. C., et al., Oncogene, 10, 291–297.), suggesting that c-ski is also estimated to be important for tumor susceptibility. Our finding that sno acts as a tumor suppressor gives a clue to understanding the physiological role of the ski/sno gene family.

EXAMPLES

Following examples illustrate the present invention more concretely, but the present invention is not limited within these examples.

Example 1

Generation of Sno Deficient Mutant Mice

The sno genomic clones were isolated from a library derived from TT2 cells by the standard plaque hybridization procedure.

A 15.0 kb HindIII-EcoRI fragment containing the exon encoding the N-terminal xxx-amino acids region of Sno was deleted from the HindIII-EcoRI fragment and replaced with a neomycin (neo) cassette derived by using the phospholipid kinase gene promoter.

To increase the frequency of gene targeting, the DT-A [diphtheria toxin-poly(A) signal] cassette for negative selection was fused to the short arm (Yagi, T. et al., Anal. Biochem., 214, 77–86, 1993).

The ES cells used were TT2 cells derived from the F1 embryo resulting from a crossbreed between C57BL/6 and CBA mice (Yagi, T. et al., Anal. Biochem., 214, 70–76, 1993). Isolation of ES clones containing sno mutation, generation of chimeras and production of heterozygous mutants were performed as described previously (Tanaka, Y., et al., Proc. Natl. Acad. Sci. USA, 94, 10215–10220, 1997). The homologous nature of the recombination was confirmed by Southern blot analysis using several restriction enzymes and several probes located either inside or outside the targeting vector as described hereinbefore. Three different primers, shown in FIG. 1(a), were used to amplify a 240 bp fragment from the wild type allele or a 120 bp fragment from the mutant allele. The mice were maintained and bred in the Division of Experimental Animal Research, Physical and Chemical Research Institute, RIKEN, Japan.

Example 2

Detection of Sno Proteins

Splenocytes were washed with PBS and resuspended in xml of lysis buffer consisting of 45 mM Tris-HCl (pH 7.4), 135 mM NaCl, 0.9% Triton X-100, 0.9% sodium deoxycholate, 0.09% SDS, 22 mM EDTA, and 1% Trasylol. After centrifugation, to xml of lysates were mixed with xml of NET/NP40 buffer [50 mM Tris-HCl (pH 7.5), 5 mM EDTA, 0.5% NP40, and 1 mg/ml BSA] containing 150 mM NaCl. xml of 100 mM of PMSF and xml of Protein G-Sepharose were added thereto, and the lysates were allowed to stand on ice for 15 minutes, and centrifuged. The supernatant was mixed with the Sno-specific monoclonal antibodies (5 mg of IgG) and the mixture was allowed to stand on ice for 2 hours. The immuno-complex was collected using 20 ml of protein G-Sepharose, washed with NET/NP40 buffer containing 0.5 and 0.25 M NaCl, NET buffer [50 Tris-HCl (pH 7.5) and 5 mM EDTA] containing 0.15 M NaCl sequentially, and developed on a 10% SDS-PAGE gel. Proteins were transferred and separated on the nitrocellulose filter, and Sno was detected using the anti-Sno monoclonal antibodies (Tokitou, F., et al., J. Biol. Chem., 274, 4425–4488, 1999) and ECL detection reagents (Amersham).

Example 3

In Vitro Culture of 2-cell Embryos and Immunostaining

M2 and M16 media were prepared (Hogan, B., et al., "Manipulating the Mouse Embryo: A Laboratory Manual." Cold Spring Harbor Laboratory, Cold Spring Harbor, N.Y.). Embryos were obtained from matings between heterozygous sno$^{+/-}$ males and females. The day a vaginal plug was found was defined as 0 day after postcoitum (dpc). Embryos were flushed out from the oviducts at 1.5 dpc using M2 medium. The embryos were cultured, individually in drops of M16 medium under paraffin oil at 37° C. in a humid atmosphere containing 5% $CO_2$. The embryos were examined periodically with a dissecting microscope. For immunostaining, embryos were fixed at room temperature for 30 minutes in freshly prepared saline buffer (pH 7.5) containing 2.5% paraformaldehyde, followed by treatment with methanol for 30 minutes and with 4% hydrogen peroxide for 30 minutes. The primary antibody-antigen complexes were detected by peroxidase conjugated anti-mouse IgG (Dako) using anti-Sno monoclonal antibodies.

Example 4

Histological Analysis and Immunohistochemistry

Various tissues were fixed in 4% paraformaldehyde, dehydrated and embedded in paraffin. Sections (5 μm) were stained with hematoxylin-eosin staining according to the standard procedures. Paraffin sections cut at 4 μm thickness were used for immunohistochemical examination. Anti-T cell receptor α and β, anti-IgM, anti-B220, and anti-CD3 antibodies were used for immunostaining.

Example 5

Analysis of Sno+/− Embryonic Fibroblasts and Splenocytes

Mouse primary embryonic fibroblasts were isolated from embryos at 13.5 or 15.5 dpc. For growth curve experiments, $10^5$ cells per well were seeded in six-well plates in DMEM containing 20% fetal bovine serum and counted. Nine independent experiments were carried out from three different MEF preparations. MEF cells were infected with Kirsten murine sarcoma virus (Ko-MuSV) and transfected with the activated K-ras oncogene (moi=10) for 48 hours. Cells ($10^5$ cells) were suspended with 1.3% methylcellulose gel and dissolved in culture medium and overlaid on an agarose bed composed of 0.53 agarose and culture medium. Colonies were counted for scoring 3 weeks after plating.

Example 6

Treatment with Carcinogen, 9,10-dimethyl-1,2-benzanthracene (DMBA)

DMBA treatments were initiated from the beginning at postnatal day 2–5 and continuing weekly thereafter by administering 50 μl of a solution containing DMBA 1.25 mg per ml acetone to the dorsal surface. Mice were monitored regularly and killed when overall health condition was deteriorated.

At first, 8–10 mice in each cohort were used for collecting histopathological informations, subsequently, the site of tumor and the site of metastatic organ were detected and specified by detailed pathological analysis.

INDUSTRIAL APPLICABILITY

The aspect of the present invention is to provide a strong clue for the screening of carcinogens, and for elucidating the mechanisms of onset or suppression of tumors. This can be done by identifying the new function of the sno gene and by developing animals lacking the sno gene and consequently having carcinogenic susceptibilities. An additional aspect of the present invention is to provide new methods for prevention and treatment of tumors by using the sno gene or complementary sequences thereof.

What is claimed is:

1. A heterozygous knockout mouse comprising a disruption in the genomic DNA fragment encoding the N-terminal amino acids of the sno gene and exhibiting one or more of tumorigenesis and propensity to ulcerative colitis, wherein the HindIII-EcoRI fragment of the sno gene exon region is replaced with a neomycin gene under the control of phospholipid kinase gene promoter.

2. A knockout mouse cell comprising a heterozygous disruption in the genomic DNA fragment encoding the N-terminal amino acids of the sno gene and exhibiting one or more of tumorigenesis and propensity to ulcerative colitis, wherein the HindIII-EcoRI fragment of the sno gene exon region is replaced with a neomycin gene under the control of phospholipid kinase gene promoter.

3. A cell according to claim 2, wherein the cell is isolated from an embryo.

4. A method for screening drug candidates comprising administering to the mouse of claim 1, a candidate drug and assessing the effects of the administration.

5. A method for screening drug candidates comprising administering to the cell of claim 2, a candidate drug and assessing the effects of the administration.

* * * * *